United States Patent
Zahynacz

(10) Patent No.: US 12,364,639 B2
(45) Date of Patent: Jul. 22, 2025

(54) WEIGHTLESS TRACTION SYSTEM

(71) Applicants: Smith & Nephew, Inc., Memphis, TN (US); Smith & Nephew Orthopaedics AG, Zug (CH); Smith & Nephew Asia Pacific Pte. Limited, Singapore (SG)

(72) Inventor: Daniel Zahynacz, Somerville, MA (US)

(73) Assignees: SMITH & NEPHEW, INC., Memphis, TN (US); SMITH & NEPHEW ORTHOPAEDICS AG, Zug (CH); SMITH & NEPHEW ASIA PACIFIC PTE. LIMITED, Singapore (SG)

( * ) Notice: Subject to any disclaimer, the term of this patent is extended or adjusted under 35 U.S.C. 154(b) by 551 days.

(21) Appl. No.: 16/972,065

(22) PCT Filed: Jun. 12, 2019

(86) PCT No.: PCT/US2019/036766
§ 371 (c)(1),
(2) Date: Dec. 4, 2020

(87) PCT Pub. No.: WO2019/241387
PCT Pub. Date: Dec. 19, 2019

(65) Prior Publication Data
US 2021/0121315 A1    Apr. 29, 2021

Related U.S. Application Data

(60) Provisional application No. 62/684,764, filed on Jun. 14, 2018.

(51) Int. Cl.
*A61H 1/00* (2006.01)
*A61B 90/57* (2016.01)
(Continued)

(52) U.S. Cl.
CPC ........... *A61H 1/0237* (2013.01); *A61B 90/57* (2016.02); *A61F 5/042* (2013.01); *A61F 5/3769* (2013.01);
(Continued)

(58) Field of Classification Search
CPC ...... A61H 1/02; A61H 1/0218; A61H 1/0222; A61H 1/0229; A61H 1/0237; A61H 1/024;
(Continued)

(56) References Cited

U.S. PATENT DOCUMENTS

| | | | | |
|---|---|---|---|---|
| 2,282,653 A | * | 5/1942 | Herzmark | A61F 5/04 602/33 |
| 2,855,200 A | * | 10/1958 | Blickman | A63B 21/169 482/130 |
| 2,997,250 A | * | 8/1961 | Collins | A61F 5/04 242/375.1 |
| 3,060,929 A | * | 10/1962 | Zivi | A63B 21/16 602/32 |

(Continued)

*Primary Examiner* — Adam Baker
(74) *Attorney, Agent, or Firm* — ArentFox Schiff LLP; Joseph M. Maraia; Marlo Schepper Grolnic

(57) ABSTRACT

A system for translating a constant traction load to an object such as a medical device or a patient includes a plurality of independently rotatable, coaxially aligned spools, each housing a constant force spring fixed at respective ends to the spool and to a rigid member, a plurality of flexible biasing members each coupled on their respective first ends to a spool and at least partially wound around the spool. A plurality of connectors are connected to the respective other ends of the biasing members, which may comprise wire rope. The connectors are configured to quickly couple to and decouple, directly or indirectly, from the object to which the traction load is being delivered. A guide provides a partial path for one or more of the biasing members to the object. A selected load may be applied by coupling one or more of the reversible couplers tensioned by the constant force springs to the object, without use of gravitational loading.

12 Claims, 3 Drawing Sheets

(51) Int. Cl.
*A61F 5/042* (2006.01)
*A61F 5/37* (2006.01)
*A61G 7/075* (2006.01)
*A61G 13/12* (2006.01)
*A61H 1/02* (2006.01)
*A61F 5/01* (2006.01)

(52) U.S. Cl.
CPC .............. *A61G 7/075* (2013.01); *A61G 13/12* (2013.01); *A61H 1/0229* (2013.01); *A61B 2090/571* (2016.02); *A61F 2005/0197* (2013.01); *A61G 2210/10* (2013.01)

(58) Field of Classification Search
CPC ...... A61H 1/0244; A61H 1/0255–0292; A61F 5/37; A61F 5/3761; A61F 5/3769; A61F 5/04; A61F 5/042; A63B 21/153; A63B 21/154; A63B 21/156; A63B 21/02–0557; A63B 21/00065; A63B 21/00061; A63B 21/025; A63B 21/023; A63B 21/0455; A63B 21/0608; A63B 21/22; A63B 21/00058; A63B 21/0069; A63B 21/04; A63B 21/045; A63B 21/055
USPC ............................................................ 602/34
See application file for complete search history.

(56) References Cited

U.S. PATENT DOCUMENTS

| | | | | |
|---|---|---|---|---|
| 3,661,150 | A * | 5/1972 | Peterssen | A61F 5/04 602/35 |
| 3,683,900 | A * | 8/1972 | Alessi | A61F 5/04 602/32 |
| 4,483,330 | A * | 11/1984 | Jacobsen | A63B 21/04 242/381 |
| 4,602,618 | A * | 7/1986 | Berze | A61H 1/0255 601/24 |
| 4,790,301 | A * | 12/1988 | Silfverskiold | A61F 5/0118 602/22 |
| 5,064,191 | A * | 11/1991 | Johnson | A63B 5/16 482/7 |
| 6,190,345 | B1 * | 2/2001 | Henderson | A61H 1/0222 602/33 |
| 7,674,216 | B1 * | 3/2010 | Bolling | A63B 21/4043 482/142 |
| 8,033,960 | B1 * | 10/2011 | Dalebout | A63B 23/03541 482/130 |
| 2009/0227929 | A1 * | 9/2009 | Gondringer | A61F 5/04 602/33 |
| 2010/0069809 | A1 * | 3/2010 | Sommers | A61F 5/04 602/32 |
| 2010/0137759 | A1 * | 6/2010 | Cook | A61H 1/0222 601/98 |

* cited by examiner

WEIGHTLESS TRACTION SYSTEM

CROSS-REFERENCE TO RELATED APPLICATIONS

This application is the U.S. national phase entry under 35 U.S.C. § 371 of International Application No. PCT/US19/36766, filed Jun. 12, 2019,entitled WEIGHTLESS TRACTION SYSTEM, which in turn claims priority to and benefit of U.S. Provisional Application No. 62/684,764, filed Jun. 14, 2018, the contents of which are incorporated herein by reference in their entirety for all purposes.

BACKGROUND

1. Technical Field

This disclosure relates to a constant tension traction device capable of developing a plurality of different tension forces, as selected by a user, such as can be beneficially applied to a medical device or an anatomical region of a patient.

2. Discussion of Related Art

The need for reliable force transferring devices suitable for use in a variety of therapeutic and/or exercise situations has been contemplated. Medical devices that are used in orthopaedic surgery sometimes require traction or suspension loads that are translated to an instrument or patient. Traction can be used to distract the bones of a limb joint (such as the wrist, ankle, elbow, knee, shoulder, or hip) during open or arthroscopic surgery, to facilitate access of surgical tools or arthroscopic instruments. Tractive forces frequently are applied during arthroscopic surgery on a limb with the aid of a traction device that utilizes continuously adjustable traction, to offer a continuous range of tractive forces. Adjustability of traction loads is critical in accommodating varying surgical requirements and patient anatomy. However, a traction device with continuously adjustable traction may not be capable of maintaining a constant tractive force on a patient's limb during the course of a surgical procedure. For example, the tractive force on the limb decreases as the limb gradually stretches under traction or if there is any gradual or sudden slippage of the limb relative to the traction device. A tractive force on the limb may increase or decrease with distinct positions of the limb. Accordingly, the traction device may require repeated readjustment to maintain a generally constant tractive force during a surgical procedure, which may prolong surgery, thereby increasing cost and risk.

Traditionally, traction or suspension mechanisms for medical devices use gravity loads (i.e., weights) or threaded displacement devices to apply traction loads during surgery. Such systems typically include rather complicated and cumbersome combinations of a framework, pulleys, ropes, and weights erected over the hospital bed. Not only are such systems cumbersome, but they are difficult and time consuming to assemble and disassemble, generally requiring external mounting to a wall or door unit. Mounting such weight bearing systems directly to the treatment table is difficult as the effectiveness of the traction device is reduced when weights bearing members are positioned too closely to the treatment table. In addition, it is difficult to either move a patient or for the patient to move himself while undergoing traction with such apparatus. Further, various protection systems have been needed with such systems to protect against or minimize shock force as the weight is raised or lowered.

There have been proposed a number of arrangements which would obviate the need for the combination of pulleys, ropes and weights. Several prior orthopedic traction devices make use of constant-force springs to apply a constant force to a patient's body, such as to a patient's spine for therapeutic purposes. However, these constant-force devices are generally not suitable for applying traction to a limb during surgery because they are not sufficiently adjustable. Thus, what is needed is an improvement over existing traction and/or suspension mechanisms for supporting a medical device or an anatomical region of a patient during surgery without the use of gravitational loads, and while allowing adjustments to the position of the device or patient without changing the applied traction load. It would be additionally desirable that such a traction device be standalone or table-mounted for easier utilization in a variety of situations.

SUMMARY

The present disclosure provides systems and methods for translating a constant load to an object requiring traction, such as an orthopaedic medical device or a portion (e.g., a limb, etc.) of a patient's anatomy, using constant-force springs. Embodiments of the system utilize series of constant force springs mounted and enclosed in independent, coaxially aligned spools on one or more arbors. Each of the spools houses a constant force spring that is secured to an inner circumferential wall of the spool at an outer (in coiled configurations) end, and fixed to a rigid arbor member that is independent from the spool at its inner coil end, thereby imparting a constant load to its respective spool. A corresponding number of relatively inelastic, flexible biasing members (e.g., wire ropes, woven fabric straps, etc.) may each be secured on a trailing end to a respective spool outer circumferential surface and be at least partially wound around the spool. At a leading end of each biasing member, a reversible connection may be made to a quick-connect device, such as a carabiner, that can be used to selectively connect the biasing members, directly or indirectly, to the medical device or patient to translate the traction or suspension load.

One embodiment of the system includes one or more guide members providing a partial pathway for wire rope biasing members from the spools to the medical device or patient. Pulling on the quick connector(s) causes the wire rope biasing member(s) to unwind, rotating the spool(s) and extending or contracting the constant force spring(s), which impart a reaction force that is translated into the traction load. Advantageously, if the medical device or patient limb (or other body part) is repositioned, the traction load applied will remain approximately constant as the wire ropes and spools adjust in length. Additional spools can be engaged by attaching their independent quick connects to the object requiring traction or, in some embodiments, an intervening single biasing member (to reduce interference that might occur between or among multiple wire ropes traversing the same pathway). The loads provided may be the same or different, spool to spool. By attaching or removing spools, the total traction load can be adjusted. Additional spools may be reversibly coupled and uncoupled as needed, while a base tractive force is applied continuously without repositioning the medical device or patient body part, thereby providing discrete adjustment of traction force while the object remains in traction. The guide may be configured with one or more pulleys and/or slides to guide the biasing members in the direction of loading.

In one embodiment, the system includes a generally vertical support and an adjustable arm that is pivotably attached to the vertical support. The vertical support may be radially and height adjustable, and the arm may pivot in two axes, providing a capability of providing the traction force from practically any location or direction. The spools may be contained in a casing that may be secured to the vertical support. The vertical support may also include a clamp for securing the system to a support surface, such as an operating table or a rail of a bed.

Thus, the system advantageously provides constant traction force without requiring gravitational loads, thereby reducing weight and size of the system, as well as health and safety risks potentially posed to surgical staff that might otherwise need to attach and remove suspended loads from traditional systems.

BRIEF DESCRIPTION OF THE DRAWING

The foregoing and other objects, features and advantages will be apparent from the following, more particular description of the embodiments, as illustrated in the accompanying figures, wherein like reference characters generally refer to identical or structurally and/or functionally similar parts throughout the different views. The figures are not necessarily to scale, emphasis instead being placed upon illustrating the principles of the embodiments, wherein.

DETAILED DESCRIPTION

The embodiments described below of weightless traction systems are merely exemplary in nature, and are in no way intended to limit the scope of the inventive concepts disclosed or their applications. Alternatives to the embodiments disclosed may be devised without departing from the scope of the disclosure.

Well-known elements of technologies associated with the embodiments will not be described in detail, or will be omitted, so as not to obscure the relevant details of the novel methods and apparatus. The word "exemplary" is used herein to mean "serving as an example, instance, or illustration." Any embodiment or component thereof described herein as "exemplary" is not necessarily to be construed as essential, preferred or advantageous over other embodiments, unless explicitly described as such. Likewise, the term "embodiment" and the descriptive language associated with each use of the term do not require that all embodiments include the discussed feature, limitation, advantage or mode of operation. For example, some of the embodiments presented focus on providing tractional force to a patient's limb, but this is not intended to limit usage of the system to that specific application. As used herein, the singular forms "a", "an" and "the" are intended to include the plural forms as well, unless the context clearly indicates otherwise. It will be further understood that the terms "comprises", "comprising", "having", "includes" and/or "including", when used herein, specify the presence of stated features, steps, elements, and/or components, but do not preclude the presence or addition of one or more other features, steps, elements, components, and/or groups thereof. Further, the phrase "based on" is intended to mean "based, at least in part, on" unless explicitly stated otherwise. The terms "force" and "load" are used interchangeably in the descriptions of embodiments below.

Figure 1:
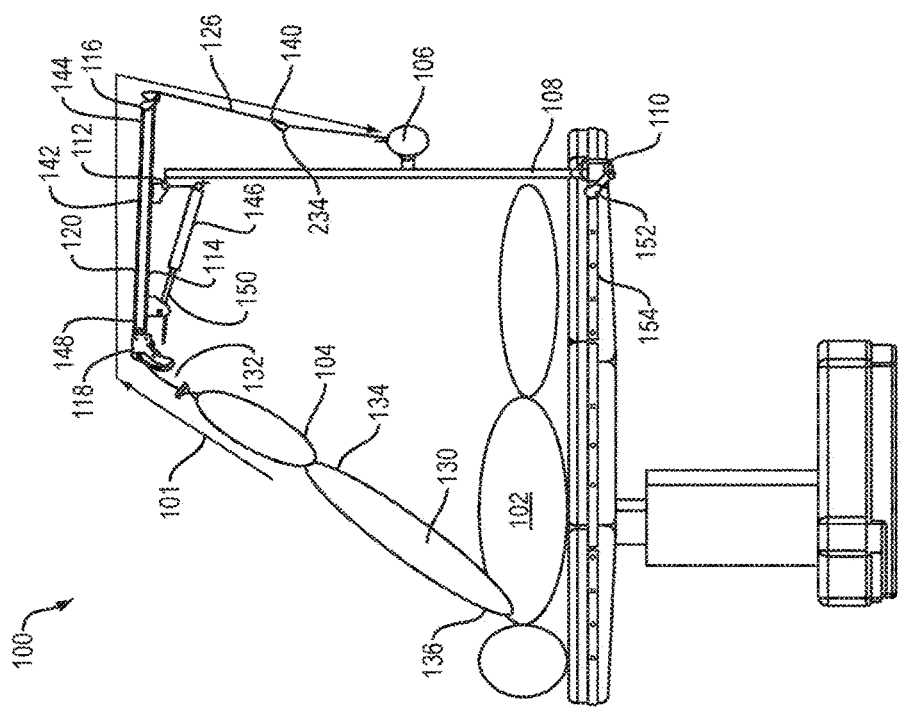
FIG. 1 is an illustration of an exemplary embodiment of a weightless traction system.

FIG. 1 shows an operating room embodiment of a system 100 for translating, directly or indirectly, an adjustably constant traction load 101 (indicated by force arrows) to an object requiring traction, such as a patient 102 or a medical device 104 (e.g., an orthopaedic medical instrument, a support assembly suitably configured to facilitate engagement with the desired portion of the patient's anatomy, etc.), without the use of gravitational loads. System 100 allows adjustments to the position of the patient 102 or medical device 104 without changing the applied traction load. System 100, and components thereof, may be manufactured from any suitable material(s), including, but not limited to, stainless steel, titanium or titanium alloy, cobalt chromium, aluminum alloys, and/or plastic, among others, including a combination thereof. These materials may be selected and/or finished to satisfy any suitable criteria, including strength, durability, appearance, and ease of use. For example, lighter-weight components may be selected to facilitate transportation and use of the traction system, while other more heavier components may be selected to provide increased stability, and heat and/or moisture-resistant materials may be selected to permit sterilization of one or more components of the traction system, among others.

System 100 may include a weightless traction accessory 106 that may be attached to a generally vertical support 108. The vertical support 108 may include a clamp 110 and a locking pivotable support 112 for a guide 114. Guide 114 may be comprised of a proximal pulley assembly 116 and a distal pulley assembly 118 and a slide 120 that provide a partial pathway 122 for one or more biasing members, such as wire ropes 124, that originate at the weightless traction accessory 106 and translate along the pathway 122 to the object (patient 102 or medical device 104) requiring support. The tractional load 101 may be provided directly to the patient 102 or medical device 104, or indirectly through intervening biasing members 126, where multiple wire ropes 124 are connected to a single intervening wire rope at a connector 128. In the embodiment shown, a limb 130 of the patient 102 is supported by system 100 during an orthopaedic surgical procedure. Medical device 104 is illustrated as a carriage or limb securement assembly affixed to the patient's limb 130 but moveable towards and away from the guide 114 to change a distance 132 therebetween. In some scenarios, medical device 104 may comprise an interventional device actively deployed by a surgeon during surgery. System 100 applies the constant tractive force 101 over a continuous range of separation, e.g., as the limb 130 is deliberately re-positioned, slips or stretches. Medical device 104 may be configured to span any suitable portion (or all) of limb 130 to which the tractive force 101 is applied. For example, medical device 104 may be configured to extend generally at least from a first region 134 to a second region 136 of limb 130 (or any other anatomical region of the body of the patient) and may span at least one joint of the limb, such as to distract bones of the joint. First region 134 may be disposed more proximally along the limb (and/or may be part of the torso) and second region 136 may be disposed more distally along the limb, or vice versa.

Figure 2A:
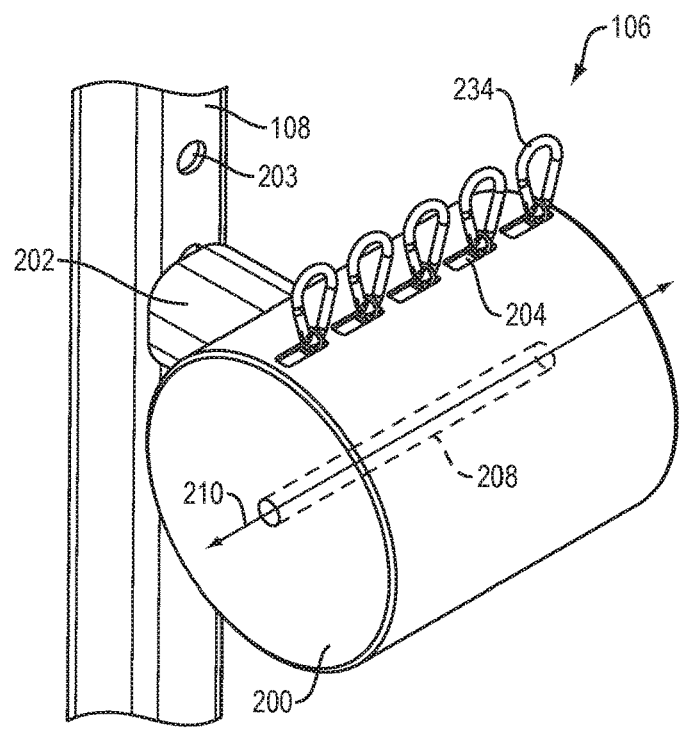
FIGS. 2A and 2B are illustrations showing exterior perspective and cross-sectional views of an exemplary embodiment of a weightless traction accessory.
Figure 2B:
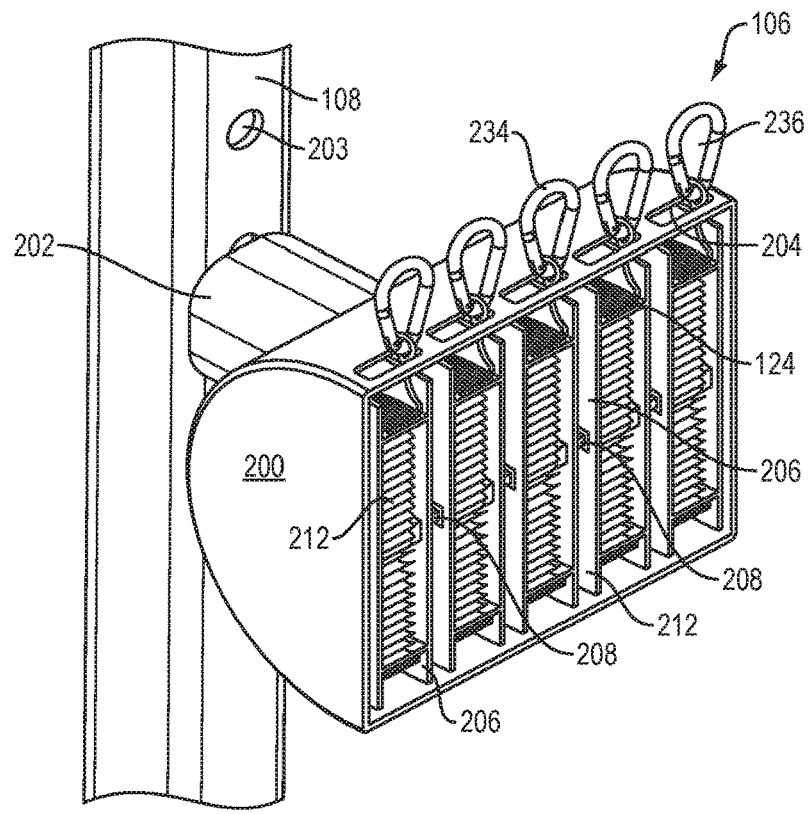

FIGS. 2A and 2B illustrate, respectively, an exterior perspective view and cross-sectional view of an embodiment of the weightless traction accessory 106. Weightless traction accessory 106 may be comprised of an exterior casing 200 that may be reversibly, rigidly secured to vertical support 108 through a connection member 202 at any of a plurality of connection holes 203 via conventional attachment means (e.g., threaded screws, locking pins, etc.). Casing 200 may include a plurality of linearly arrayed slot openings 204 oriented vertically, generally parallel to vertical support 108 to permit easy extension and retraction of wire ropes 124.

Figure 3:
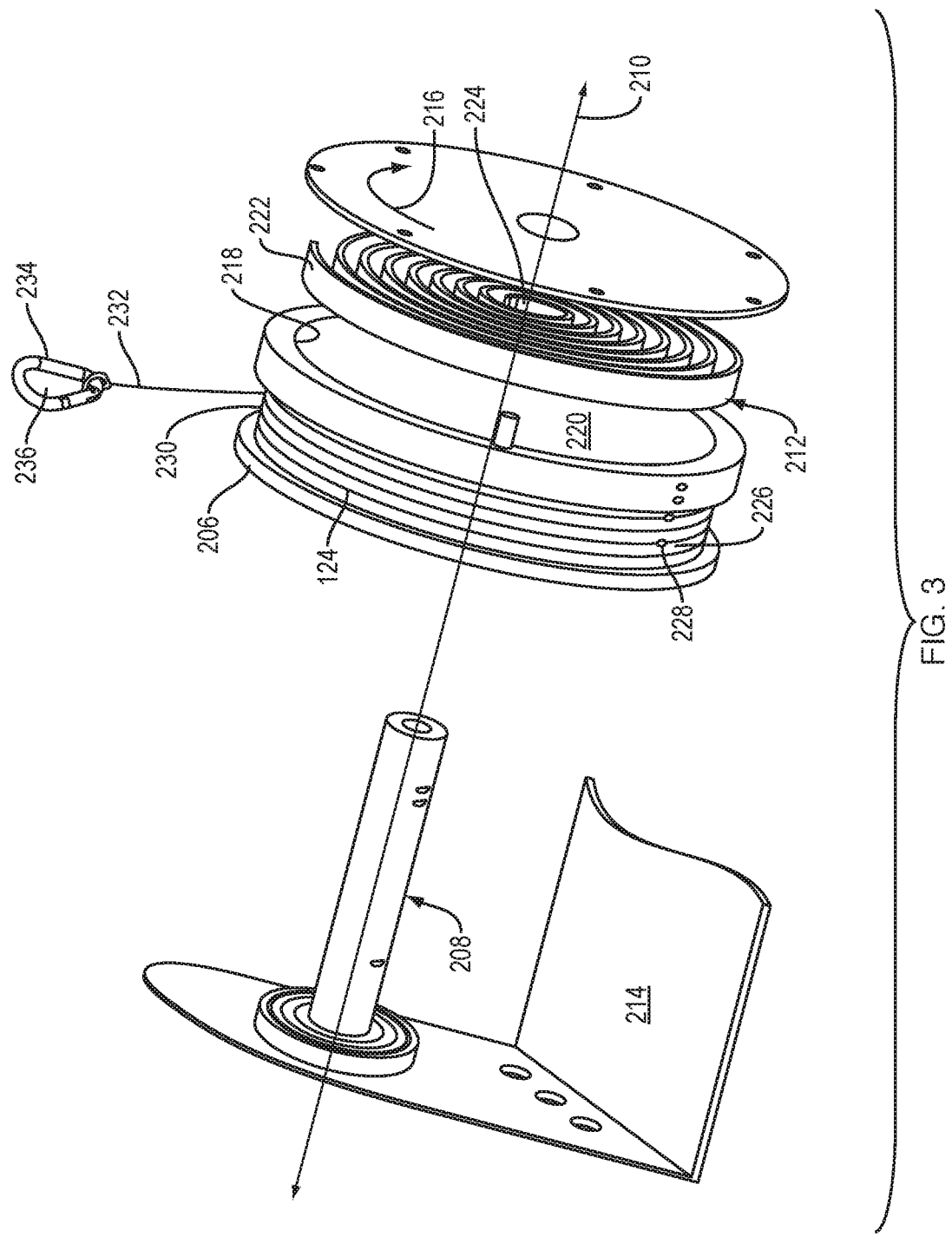
FIG. 3 is illustration of an exploded view of an embodiment of a single spool assembly.

Casing 200 may have a cylindrical body reflective of the casing's contents, which include a plurality of independently rotatable, coaxially aligned spools 206. FIG. 3 illustrates an exploded view of an embodiment of a single spool 206. Each spool 206 is rotatably supported in one embodiment by a single arbor 208 held immobile by the casing 200 for rotation about a central rotation axis 210. The arbor 208 operatively engages constant-force springs 212 and may be integral to the casing 200, such that the spools 206 are supported rotatably by the casing 200 through the arbor 208. In an alternative embodiment, each spool 206 may be separately housed in coaxially aligned carriage assembly 214 internal to the casing 200, such that each spool 206 is independently rotatably supported by the carriage assembly 214 through a distinct, coaxially aligned arbors. The rotation of spool 206 about the arbor 208 results in an applied tension from the constant force spring 212 contained therein, when spool 206 rotated in a rotation direction 216 that attempts to extend the constant force spring 212.

Each constant force spring 212 may comprise a flat coil of resilient material, such as a coiled (rolled) ribbon, that is rigidly secured to a portion 218 of an inner circumferential wall 220 the spool 206 at an outer end 222 of the coiled constant force spring 212 and may be secured to the arbor 208 at an inner end 224 of the coiled spring 212. Each spring 212 may contact the arbor 208 or may optionally be spaced from the arbor 208 by a bearing (not shown) that may reduce friction, thereby reducing any lag in application of tractive force as the wire rope 124 is extended and/or retracted from spool 206. Any suitable bearing may be used to reduce friction between the spring 212 and the arbor 208. Exemplary bearings that may be suitable include ball bearings, needle roller bearings, bushings, or a combination thereof, among others. The constant force springs 212 may have similar or distinct spring constants, to correspondingly exert similar or different magnitudes of tractive force.

Wound multiple times around each spool 206 is one of the relatively inelastic, flexible biasing members, which may be straps of woven fabric or lengths of wire rope 124. Each wire rope 124 is secured on a trailing end 226 to an exterior contact point 228 on an exterior circumferential surface 230 of the corresponding spool 206. A leading end 232 of each length of wire rope 124 may be threaded through one of the slot openings 204 of the casing 200 and attached to a connector 234. The slot openings 204 are configured with dimensions that do not impede the motion of the wire rope 124 there through, but narrow enough to preclude the connector 234 from entering the casing 200. The connector 234 may be sized and shaped to be engaged between a user's thumb and fingers.

When the constant force spring 212 is rotatably supported, it will rotate about the central rotation axis 210 as a length of wire rope 124 unwinds from (or winds onto) the spool 206. The spring 212 is biased toward its fully coiled configuration, and provides the constant tractive load 101 on the outer end 222 over a continuous range of lengths of the wire rope 124.

Each quick connector 234 is affixed to a corresponding leading end 232 of wire rope 124, and may comprise a reversible fastener, such as a carabiner, configured for quick coupling and decoupling. The quick connector 234 may be a distinct component from the wire rope 124, or alternatively may be integrally formed with the leading end 232 of the wire rope 124, such as in the form of a hole 236 configured to be received on a pin or hook.

With reference again to FIG. 1, it will be readily appreciated that the wire rope connectors 234 may be configured, in various embodiments, to connect directly to a patient 102 or medical device 104, or to an intervening length of wire rope 126 (e.g., to reduce the number of ropes traversing guide 114) by means of a connector ring 140 (or eyelet, hook, etc.), or other complementary mating structure to which the quick connectors 234 may reversibly couple. Steel wires for wire ropes are normally made of non-alloy carbon steel with a carbon content of 0.4 to 0.95%. The very high strength of the rope wires enables wire ropes to support large tensile forces and to allow the flexing needed for wrapping around the spools 206 and through the pathway 122 to the patient 102.

The guide 114 of system 100 may comprise an adjustable slide, rail or tube, etc., having a curvature that accommodates relatively frictionless translation of one or more lengths of wire rope 124. Guide 114 may comprise an adjustable arm supported by locking pivot support 112 fixedly connected near the top end of vertical support 108 at a middle portion 142 or proximal end 144 of the guide 114, and by a gas spring 146 or other adjustable load bearing element connecting a distal end 148 of the guide to the vertical support 108 below the locking pivot support 112. The gas spring 146 may be of a conventional type, with a suitable outer housing and an inner rod 150 telescopically received within the outer housing. The gas spring 146 may be configured such that the telescoping rod 150 is in an extended position relative to the outer housing when at rest, and may be configured with an appropriate adjustment member such as a pin, clamp, or other locking mechanism, such as a rod with suitable detent, which will permit secure but movable engagement for adjusting the orientation of gas spring 146. The gas spring 146 has suitable means for attaching the distal end of the inner telescoping rod 150 to a distal section of the guide 114. The attachment means may be any suitable bolt, clamp, or other locking mechanism such as a pin with a suitable detent. The gas spring 146 can be of any suitable rating (e.g., 10 to 250 pounds) needed according to the configuration and guide-supporting force required.

Vertical support 108 is adjustable radially and in height through use of the locking clamp 110, which allows compensation for anatomical variations in individual patients. In alternative embodiment (not shown), vertical support 108 may comprise a main arm having a connected by an elbow joint to the proximal end 144 of the guide 114, which in such embodiment comprises an articulating arm. The locking clamp 110 may be spring biased to its gripping position, so that it is only maintained in its releasing position by actuating (pushing or pulling) and holding the lever assembly 152, thereby ensuring that the vertical support 108 is held in a fixed position at all times other than when it is desired to adjust the relative position of the system with respect to the patient. The lever assembly 152 may be designed to ensure that it may be easily reached and actuated by a user standing anywhere along the head end or along either side of a support surface 154.

Support surface 154 may comprise a stationary support such as a surgical table or hospital bed. Another clamp and a mechanical shoulder joint may be utilized to achieve the angular motion provided at locking pivotable support 112 between the vertical support 108 and the generally horizontal guide 114. A proximal end of the guide may be attached to the horizontal clamp by means of a shoulder joint, which preferably provides a rotational capability through a 360° range. The guide 114 may also be equipped with a telescoping or fine linear adjustment mechanism for small adjustments in the length of guide 114 after all other positioning has been effected.

In one embodiment, the wire rope pathway 122 may originate at the weightless traction accessory 106, traverse the proximal pulley assembly 116 disposed at the proximal end 144, rail portion, and the distal pulley assembly 118 affixed to the distal end 148 of the guide 114. Lengths of wire rope 124 extend through the pulley assemblies 116, 118 and are moveable relative thereto, changing directions of the transferred traction load as a result. The proximal pulley assembly 116 is mounted such that the angle between the weightless traction accessory 106 and the guide 114 may be less than 90°, for more effective translation of the traction force. A direct or indirect connection may then be made to the anatomical part of the patient or to the medical device requiring traction. As noted, intervening lengths of wire rope, with associated quick connectors, may be utilized in various embodiments.

In operation, the vertical support 108 and guide 114 may be adjusted in spatial relation to the patient's limb or the medical device before or during application of the tractive load 101. For example, be guide may be pivoted with respect to the vertical support, and then fixed in the desired position. Alternatively, or in addition, the length of the guide 114 may be adjusted, such as by pivoting a more proximal section of the guide relative to a more distal section and then fixing the pivotal position of the proximal section with respect to distal section. The desired tractive load 101 may then be applied by selectively coupling one or more of the reversible couplers 234 directly or indirectly to the patient or medical device. Individual coupling or uncoupling constant force springs 212 discretely adjusts the tractive load 101. Additional or fewer wire ropes 124 may be placed in the coupled configuration when extended, such that a base tractive force applied to the limb may be increased or decreased by the corresponding springs 212. These adjustments may be made while the limb remains in traction. For example, a supplementary wire rope 124 may be placed in the coupled configuration while already connected wire ropes continuously apply a base tractive load to the limb, without repositioning the limb and/or repositioning the already connected wire ropes 124. When the patient 102 is coupled (directly or indirectly) to the one or more of the reversible couplers 234, any repositioning of the patient or device results in a negligible change in the constant force being operatively provided.

In some embodiments (not shown), the rotation axes about which the constant-force springs 212 rotate when the wire ropes 124 extend or retract may not necessarily be coaxial. For example, at least two or all of the rotation axes may be parallel to one another, such as with the constant-force springs arranged generally along a line. Alternatively, or in addition, at least two of the rotation axes may be transverse to each other, such as at least substantially orthogonal to one another. In some embodiments, the constant-force springs may include a first pair of springs arranged transversely or at least substantially orthogonally to a second pair of springs. Arrangement of constant-force springs around an axis may be advantageous in some cases to balance the forces exerted by the springs. In other embodiments, the constant force springs may be configured as torsional and/or other spring types instead of, or in addition to, the flat coiled springs described above.

Whereas many alterations and modifications of the disclosure will no doubt become apparent to a person of ordinary skill in the art after having read the foregoing description, it is to be understood that the particular embodiments shown and described by way of illustration are in no way intended to be considered limiting.

The invention claimed is:

1. A system for translating a constant load to an object requiring traction, comprising:
a plurality of independently rotatable, coaxially aligned spools rotatable about a same rigid member that is independent from the spools, each one of the plurality of spools housing a constant force spring that is fixed to an inner circumferential wall of the spool at a first end, and fixed to the rigid member at a second end;
a corresponding plurality of relatively inelastic, flexible biasing members, each coupled on a first end to an exterior contact point on an exterior circumferential surface of one of the spools and at least partially wound around the spool associated with the constant force spring;
a corresponding plurality of connectors, each connector attached to a second end of one of the relatively inelastic, flexible biasing members, and each including a reversible couplers configured to quickly couple to and decouple from the object; and
a guide mounted on a vertical support, the guide including one or more slides extending between the vertical support and the object, the guide providing a partial path for one or more of the biasing members extending through a length of the one or more slides to the object;
wherein a desired load may be applied to the object by selectively coupling one or more of the reversible couplers to the object, such that when the object is coupled to the one or more of the reversible couplers, any repositioning of the object from a first position to a second position results in a negligible change in the desired load being operatively translated to the object through the one or more reversible couplers and associated one or more flexible biasing members from the associated one or more constant force springs;
wherein each one of the plurality of spools is housed in a same casing rigidly affixed to the vertical support adjacent the one or more slides such that a user can selectively couple the one or more of the reversible couplers to the object to discretely adjust the desired load on the object, the casing formed as a closed body disposed about the plurality of spools; and
wherein an outer surface of the casing defines a plurality of slots, each one of the slots configured to allow extension and retraction of a corresponding one of the biasing members through the slot.

2. The system of claim 1, wherein the desired load is achieved without use of gravitational loading.

3. The system of claim 1, wherein the object comprises a medical device configured to facilitate engagement with an anatomical region of a patient.

4. The system of claim 1, wherein the object comprises an anatomical region of a patient.

5. The system of claim 1, further comprising an adjustable arm pivotably affixed to the vertical support.

6. The system of claim 1, wherein the vertical support is adjustable in height.

7. The system of claim 1, further comprising a clamp for securing the vertical support to a support surface.

8. The system of claim 1, wherein the guide, connectors and biasing members are configured for use in orthopaedic surgery.

9. The system of claim 1, wherein the reversible couplers comprise carabiners.

10. The system of claim 1, wherein the partial path for the one or more of the biasing members provided by the guide traverses one or more pulley assembly.

11. The system of claim 1, wherein the casing is cylindrical.

12. The system of claim 1, wherein each one of the slots is arranged such that a long axis of each one of the slots extends along a long axis of the casing and a width of an outer boundary of each one of the slots is selected to preclude a connector from entering the casing.

* * * * *